(12) United States Patent
Baek et al.

(10) Patent No.: US 9,962,625 B2
(45) Date of Patent: May 8, 2018

(54) PROCESS FOR CONTINUOUSLY RECOVERING (METH)ACRYLIC ACID AND APPARATUS FOR THE PROCESS

(71) Applicant: LG CHEM, LTD., Seoul (KR)

(72) Inventors: Se Won Baek, Daejeon (KR); Jong Hun Song, Daejeon (KR); Sul Hee Yoo, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days. days.

(21) Appl. No.: 14/903,206

(22) PCT Filed: Jul. 21, 2014

(86) PCT No.: PCT/KR2014/006608
§ 371 (c)(1),
(2) Date: Jan. 6, 2016

(87) PCT Pub. No.: WO2015/012551
PCT Pub. Date: Jan. 29, 2015

(65) Prior Publication Data
US 2016/0376214 A1    Dec. 29, 2016

(30) Foreign Application Priority Data

Jul. 22, 2013 (KR) .................. 10-2013-0086215
Jul. 18, 2014 (KR) .................. 10-2014-0091243

(51) Int. Cl.
*B01D 3/14* (2006.01)
*C07C 51/48* (2006.01)
(Continued)

(52) U.S. Cl.
CPC .......... *B01D 3/143* (2013.01); *B01D 11/0488* (2013.01); *C07C 51/42* (2013.01);
(Continued)

(58) Field of Classification Search
None
See application file for complete search history.

(56) References Cited

U.S. PATENT DOCUMENTS

| 4,956,493 A * | 9/1990 | Ueoka ..................... C07C 67/08 |
| | | 560/208 |
| 6,084,127 A | 7/2000 | Sakamoto et al. |

(Continued)

FOREIGN PATENT DOCUMENTS

| JP | 2009-242285 A | 10/2009 |
| JP | 2009-263348 A | 11/2009 |

(Continued)

OTHER PUBLICATIONS

Machine translation of Shinji (JP 2009242285, published on Oct. 22, 2009 and of record in the IDS filed on Jan. 6, 2016), p. 1-25.*

(Continued)

*Primary Examiner* — Jafar Parsa
*Assistant Examiner* — Amy C Bonaparte
(74) *Attorney, Agent, or Firm* — Dentons US LLP

(57) ABSTRACT

This disclosure relates to a method for continuous recovery of (meth)acrylic acid and an apparatus used for the recovery method. The method of continuous recovery of (meth) acrylic acid according to the present invention may remarkably reduce the amount of extraction solvent used and energy consumption of the total process, and minimize polymerization of (meth)acrylic acid in the recovery process, thus enabling stable recovery of (meth)acrylic acid and operation of a continuous process.

7 Claims, 1 Drawing Sheet

(51) Int. Cl.
    *B01D 11/04*     (2006.01)
    *C07C 51/44*     (2006.01)
    *C07C 51/42*     (2006.01)
    *C07C 51/43*     (2006.01)

(52) U.S. Cl.
    CPC .............. *C07C 51/43* (2013.01); *C07C 51/44* (2013.01); *C07C 51/48* (2013.01)

(56) References Cited

U.S. PATENT DOCUMENTS

| | | |
|---|---|---|
| 8,246,790 B2 | 8/2012 | Baek et al. |
| 2015/0203431 A1 | 7/2015 | Baek et al. |

FOREIGN PATENT DOCUMENTS

| | | |
|---|---|---|
| KR | 10-1981-0001298 B1 | 10/1981 |
| KR | 10-1983-0000024 B1 | 1/1983 |
| KR | 10-0349602 B1 | 8/2002 |
| KR | 10-0371759 B1 | 1/2003 |
| KR | 10-0375780 B1 | 2/2003 |
| KR | 10-0584677 B1 | 5/2006 |
| KR | 10-2009-0041355 A | 4/2009 |
| KR | 10-2010-0107029 A | 10/2010 |
| KR | 10-1011769 B1 | 1/2011 |
| WO | 2013/037134 A1 | 3/2013 |

OTHER PUBLICATIONS https://web.archive.org/web/20141013195004/http://www.che.utah.edu/~sutherland/3603Notes/AbsorptionStripping.pdf, downloaded on Apr. 25, 2017, available online since at least Oct. 13, 2014, p. 1-25.*

English language translation of JP 2009/242285, obtained Dec. 2016, p. 1-47.*

English language translation of JP JP 2009/263348, obtained Mar. 2017, p. 1-48.*

* cited by examiner

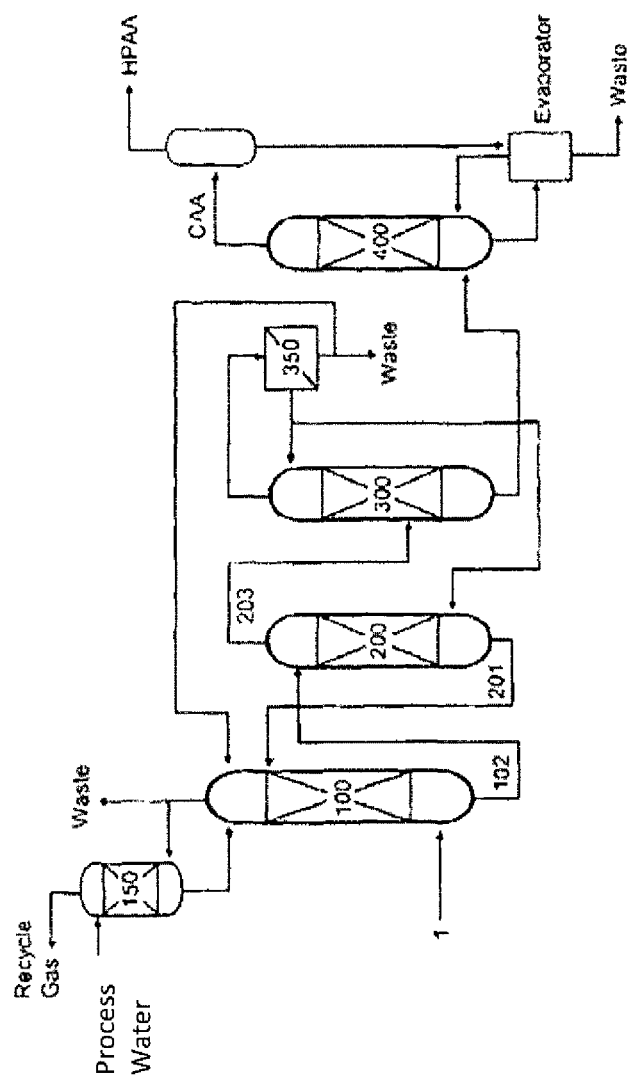

PROCESS FOR CONTINUOUSLY RECOVERING (METH)ACRYLIC ACID AND APPARATUS FOR THE PROCESS

This application is a National Stage Entry of International Application No. PCT/KR2014/006608, filed Jul. 21, 2014, and claims the benefit of and priority to Korean Application No. 10-2013-0086215, filed Jul. 22, 2013 and Korean Application No. 10-2014-0091243, filed Jul. 18, 2014, all of which are incorporated herein by reference in their entirety for all purposes as if fully set forth herein.

TECHNICAL FIELD

The present invention relates to a method of continuous recovery of (meth)acrylic acid and an apparatus for the method.

BACKGROUND OF ART (Meth)acrylic acid is generally prepared by gas phase oxidation of propane, propylene, (meth)acrolein, and the like in the presence of a catalyst. For example, propane, propylene, and the like are converted to (meth)acrylic acid through (meth)acrolein by gas phase oxidation in the presence of an appropriate catalyst in a reactor, and a reaction product mixed gas including (meth)acrylic acid, non-reacted propane or propylene, (meth)acrolein, an inert gas, carbon dioxide, water vapor, and various organic by-products (acetic acid, heavies, and the like) is obtained in the back end of the reactor.

The (meth)acrylic acid-containing mixed gas contacts an absorption solvent such as process water in a (meth)acrylic acid absorption tower, and is recovered as a (meth)acrylic acid aqueous solution. Further, (meth)acrylic acid-stripped insoluble gas is recycled for a synthesis reaction of (meth)acrylic acid, and a part thereof is incinerated and discharged. The (meth)acrylic acid aqueous solution is distilled and purified to obtain (meth)acrylic acid.

Meanwhile, various methods of controlling process conditions or a process sequence and the like to improve the recovery efficiency of (meth)acrylic acid have been suggested. Representatively, as a method for separating water and acetic acid from the (meth)acrylic acid aqueous solution obtained in the (meth)acrylic acid absorption tower, an azeotropic distillation method using a hydrophobic solvent in a distillation column is known. The azeotropic distillation method is a method of effectively recovering (meth)acrylic acid by recovering acetic acid, which is a main by-product of (meth)acrylic acid synthesis, together with water, through a distillation process using a hydrophobic solvent.

Particularly, the inventors have suggested in Korean Laid-Open Patent Publication No. 2009-0041355 that a hydrophobic solvent is used in a distillation column, and acetic acid containing waste water recovered from the upper part of a distillation column is recycled to a (meth)acrylic acid absorption tower and reused. As such, the azeotropic distillation method in a distillation column has the effects of reducing the amount of waste water, and simultaneously, effectively inhibiting inflow of organic substances, and simplifying the subsequent purification step.

However, the azeotropic distillation method and previously disclosed recovery methods of (meth)acrylic acid have problems in that a large amount of energy is consumed in the process of distilling a (meth)acrylic acid aqueous solution, treatment load in the distillation process is high, and a polymer is produced due to polymerization of (meth)acrylic acid to render normal operation impossible, thus lowering stability of a process operation.

DETAILED DESCRIPTION OF THE INVENTION

Technical Problem

It is an object of the present invention to provide a method for continuous recovery of (meth)acrylic acid that may remarkably reduce energy consumption and yet enables stable recovery of (meth)acrylic acid and operation of a continuous process.

It is another object of the present invention to provide an apparatus that can be used for the continuous recovery of (meth)acrylic acid.

Technical Solution

According to the present invention, provided is a method for continuous recovery of (meth)acrylic acid including:

an absorption process wherein a mixed gas including (meth)acrylic acid, organic by-products, and vapor, which is produced by a synthesis reaction of (meth)acrylic acid, is contacted with water to obtain a (meth)acrylic acid aqueous solution;

an extraction process wherein the (meth)acrylic acid aqueous solution obtained through the absorption process is contacted with an extraction solvent in an extraction column to obtain a (meth)acrylic acid extract solution and a raffinate solution; and a distillation process wherein a feed including the (meth)acrylic acid extract solution obtained through the extraction process is distilled to obtain (meth)acrylic acid, wherein the raffinate solution obtained through the extraction process is fed to at least one point corresponding to 10 to 30% from the uppermost part of the (meth)acrylic acid absorption tower, and the weight ratio of the extraction solvent to the (meth)acrylic acid aqueous solution fed to the extraction column is greater than 0.3 and less than 1.0.

According to the present invention, the absorption process may be conducted in a packed column type of (meth)acrylic acid absorption tower, and the raffinate solution obtained through the extraction process may be fed to at least one point corresponding to 10 to 30% from the uppermost part compared to the total packing height of the (meth)acrylic acid absorption tower.

According to the present invention, the absorption process may be conducted in a multistage tray type of (meth)acrylic acid absorption tower, and the raffinate solution obtained through the extraction process may be fed to at least one point corresponding to 10 to 30% from the uppermost stage compared to the total stage number of the (meth)acrylic acid absorption tower.

The extraction solvent may be a hydrophobic solvent having a boiling point of 10 to 120° C.

The raffinate solution obtained through the extraction process may include 30 to 60 wt % of (meth)acrylic acid, 30 to 60 wt % of an extraction solvent, 3 to 10 wt % of water, and a remaining amount of organic by-products.

Further, the raffinate solution obtained through the extraction process may include (meth)acrylic acid in the content of 15 wt % or less.

Meanwhile, according to the present invention, an apparatus for continuous recovery of (meth)acrylic acid is provided, including:

a (meth)acrylic acid absorption tower (100) equipped with a mixed gas inlet to which mixed gas including (meth) acrylic acid, organic by-products, and vapor, which is produced by a synthesis reaction of (meth)acrylic acid, is fed, and an aqueous solution outlet from which a (meth)acrylic acid aqueous solution obtained by contact of the mixed gas with water is discharged;

a (meth)acrylic acid extraction column (200) equipped with an aqueous solution inlet connected with the aqueous solution outlet of the absorption tower (100) through an aqueous solution transfer line (102), an extract outlet from which the (meth)acrylic acid extract solution obtained by contact of the introduced (meth)acrylic acid aqueous solution with an extraction solvent is discharged, and a raffinate outlet from which the raffinate solution is discharged; and a distillation column (300) equipped with an extract inlet connected with the extract outlet of the extraction column (200) through an extract transfer line (203), and a (meth) acrylic acid outlet from which (meth)acrylic acid obtained by distillation of the introduced extract solution is discharged, wherein the raffinate outlet of the extraction column (200) is connected to at least one point corresponding to 10 to 30% from the uppermost part of the absorption tower (100) through a raffinate transfer line (201), and the apparatus is operated such that the weight ratio of the extraction solvent to the (meth)acrylic acid aqueous solution fed to the extraction column (200) is greater than 0.3 and less than 1.0.

According to the present invention, the (meth)acrylic acid absorption tower (100) may be a packed column type of absorption tower, and the raffinate outlet of the extraction column (200) may be connected to at least one point corresponding to 10 to 30% from the uppermost part compared to the total packing height of the absorption tower (100) through a raffinate transfer line (201).

Further, according to the present invention, the (meth) acrylic acid absorption tower (100) may be a multistage tray type of absorption tower, and the raffinate outlet of the extraction column (200) may be connected to at least one point corresponding to 10 to 30% from the uppermost stage compared to the total stage number of the absorption tower (100) through a raffinate transfer line (201).

Advantageous Effects

The method of continuous recovery of (meth)acrylic acid according to the present invention may remarkably reduce the amount of extraction solvent used and energy consumption of the total process, and minimize polymerization of (meth)acrylic acid in the recovery process, thus enabling stable recovery of (meth)acrylic acid and operation of a continuous process.

BRIEF DESCRIPTION OF THE DRAWINGS

The FIGURE schematically shows the method and apparatus for continuous recovery of (meth)acrylic acid according to one embodiment of the invention.

REFERENCE NUMERALS

1: (meth)acrylic acid containing mixed gas
100: (meth)acrylic acid absorption tower
102: (meth)acrylic acid aqueous solution transfer line
150: acetic acid absorption tower
200: (meth)acrylic acid extraction column
201: raffinate transfer line
203: extract transfer line
300: distillation column
350: phase separation tank
400: heavies separation tower
CAA: crude (meth)acrylic acid
HPAA: high purity (meth)acrylic acid

DETAILED DESCRIPTION OF THE EMBODIMENTS

Hereinafter, a method of continuous recovery of (meth) acrylic acid and a recovery apparatus according to the embodiments of the invention will be explained.

First, the technical terms used herein are only to mention specific embodiments, and are not intended to limit the invention. Further, singular forms used herein include plural forms, unless they have clearly opposite meanings. Further, the meaning of 'comprising' as used herein embodies a specific property, area, integer, step, operation, element, or component, and it does not exclude the addition of other specific properties, areas, integers, steps, operations, elements, or components.

Unless otherwise described, terms used herein are defined as follows.

The term '(meth)acrylic acid' generally refers to acrylic acid, methacrylic acid, or a mixture thereof.

The term '(meth)acrylic acid-containing mixed gas' generally refers to a mixed gas that may be produced when (meth)acrylic acid is prepared by gas phase oxidation. As a non-limiting example, the (meth)acrylic acid-containing mixed gas may be obtained by gas phase oxidation of at least one compound selected from the group consisting of propane, propylene, butane, i-butylene, t-butylene, and (meth) acrolein ('raw material compound') in the presence of a catalyst, wherein the (meth)acrylic acid-containing mixed gas may include (meth)acrylic acid, non-reacted raw material compounds, (meth)acrolein, an inert gas, carbon monoxide, carbon dioxide, water vapor, and various organic by-products (acetic acid, light ends, heavies, and the like), and the like.

Herein, the term 'light ends' or 'heavies' commonly refers to a kind of by-products that can be produced in the process of preparing and recovering aimed (meth)acrylic acid, and has lower or higher molecular weight than (meth)acrylic acid. Further, poorly water-soluble floating material formed by the organic by-products is referred to as 'scum'.

The term '(meth)acrylic acid aqueous solution' refers to an aqueous solution containing (meth)acrylic acid, and for example, it may be obtained by contacting the (meth)acrylic acid-containing mixed gas with an absorption solvent including water.

The term 'feed' refers to a liquid mixture containing a solute to be extracted, and it may be a mixture of a solute that is soluble in an extraction solvent and inert material that is not soluble in an extraction solvent. Herein, if the extraction solvent is added to the feed, the solute is dissolved in the extraction solvent from the feed by mass transfer. Thereby, the extraction solvent in which a significant amount of solutes is dissolved forms an extract solution, and the feed that is deprived of a significant amount of solutes forms a raffinate solution.

Meanwhile, in liquid-liquid extraction using agitated columns such as a Karr-type column and a Scheibel-type column, a relatively light phase is fed to the lower stage of the extraction column and a relatively heavy phase is fed to the upper stage of the extraction column. Further, extraction is progressed by the contact of materials fed to the extraction column, to obtain a light phase and a heavy phase of new compositions.

The light phase of the new composition obtained through the extraction process is obtained through the upper outlet of the extraction column, and the heavy phase of the new composition is obtained through the lower outlet of the extraction column.

In general, the heavy phase of the new composition obtained through the extraction process, before being discharged to the lower outlet of the extraction column, remains stationary at the lower part of the extraction column, and a part thereof is discharged to the lower outlet of the extraction column. Herein, the section of the extraction column in which the heavy phase remains stationary is referred to as 'lower stationary section' (or 'stationary section of heavy phase').

For example, in the process of extracting (meth)acrylic acid included in a (meth)acrylic acid aqueous solution using an extraction solvent, the (meth)acrylic acid aqueous solution that is in a relatively heavy phase is fed to the upper stage of the extraction column, and the extraction solvent that is in a relatively light phase is fed to the lower stage of the extraction column. Further, extraction is progressed by the contact thereof, and an extract solution in which a significant amount of (meth)acrylic acid is dissolved and a raffinate solution that is deprived of a significant amount of (meth)acrylic acid are obtained. Herein, the extract solution that is in a relatively light phase is obtained through the upper outlet of the extraction column, and the raffinate solution that is in a relatively heavy phase is obtained through the lower outlet of the extraction column.

Hereinafter, referring to the attached drawing, a specific embodiment of the invention will be explained in detail so that one of ordinary knowledge in the art may easily practice it. However, the present invention may be embodied in various forms, and is not limited to the examples.

Meanwhile, during studies on a method of continuous recovery of (meth)acrylic acid, it was confirmed that the previously disclosed recovery method of (meth)acrylic acid through azeotropic distillation consumes a large amount of energy in the distillation process, and has lowered process stability due to the production of a polymer by polymerization of (meth)acrylic acid during the distillation process.

Thus, as a result of continuous studies, the inventors confirmed that if a (meth)acrylic acid extraction process is introduced between a (meth)acrylic acid absorption process and a distillation process as shown in the FIGURE, an operation load of the distillation process may be remarkably lowered. Furthermore, it was confirmed that if a raffinate solution of the extraction process is fed to a specific point of a (meth)acrylic acid absorption tower, and simultaneously the weight ratio of an extraction solvent to a (meth)acrylic acid aqueous solution in the extraction process is controlled, energy consumption compared to recovery rate of (meth)acrylic acid may be remarkably lowered, and more stable operation of a continuous process is enabled.

I. A Method of Continuous Recovery of (Meth)Acrylic Acid

According to one embodiment of the invention, a method for continuous recovery of (meth)acrylic acid is provided, including:

an absorption process wherein a mixed gas including (meth)acrylic acid, organic by-products, and vapor, which is produced by a synthesis reaction of (meth)acrylic acid, is contacted with water to obtain a (meth)acrylic acid aqueous solution;

an extraction process wherein the (meth)acrylic acid aqueous solution obtained through the absorption process is contacted with an extraction solvent in an extraction column to obtain a (meth)acrylic acid extract solution and a raffinate solution; and a distillation process wherein a feed including the (meth)acrylic acid extract solution obtained through the extraction process is distilled to obtain (meth)acrylic acid, wherein the raffinate solution obtained through the extraction process is fed to at least one point corresponding to 10 to 30% from the uppermost part of the (meth)acrylic acid absorption tower, and the weight ratio of the extraction solvent to the (meth)acrylic acid aqueous solution fed to the extraction column is greater than 0.3 and less than 1.0.

Hereinafter, referring to the FIGURE, each process that can be included in the embodiment of the invention will be explained.

(Absorption Process)

An absorption process is a process for obtaining a (meth)acrylic acid aqueous solution, and it may be conducted by contacting a (meth)acrylic acid-containing mixed gas obtained through the synthesis reaction of (meth)acrylic acid with an absorption solvent including water.

As a non-limiting example, the synthesis reaction of (meth)acrylic acid may be conducted by the oxidation reaction of at least one compound selected from the group consisting of propane, propylene, butane, isobutylene, and (meth)acrolein in the presence of a gas phase catalyst. Herein, the gas phase oxidation reaction may be progressed using a gas phase oxidation reactor of a common structure and under common reaction conditions. As the catalyst for the gas phase oxidation reaction, common catalysts may be used, and for example, catalysts suggested in Korean Registered Patent No. 0349602 and No. 037818 and the like may be used. In the (meth)acrylic acid-containing mixed gas produced by the gas phase oxidation reaction, in addition to the desired product (meth)acrylic acid, non-reacted raw material compounds, intermediate (meth)acrolein, an inert gas, carbon dioxide, vapor, and various organic by-products (acetic acid, light ends, heavies, and the like) may be included.

Further, referring to the FIGURE, the (meth)acrylic acid aqueous solution may be obtained by feeding a (meth)acrylic acid-containing mixed gas (1) to a (meth)acrylic acid absorption tower (100) to contact it with an absorption solvent including water.

Herein, the kind of the (meth)acrylic acid absorption tower (100) may be determined considering contact efficiency of the mixed gas (1) with the absorption solvent, and the like. As non-limiting examples, the (meth)acrylic acid absorption tower (100) may be a packed column tower or a multistage tray tower. Inside the packed tower, a filler such as a Raschig ring, a pall ring, a saddle, gauze, structured packing, and the like may be applied.

Further, considering the efficiency of the absorption process, the mixed gas (1) may be fed to the lower part of the absorption tower (100), and the solvent including water may be fed to the upper part of the absorption tower (100).

The absorption solvent may include water such as tap water, deionized water, and the like, and it may include recycled process water introduced from other processes (for example, an aqueous phase recycled from an extraction process and/or a distillation process). Further, in the absorption solvent, a trace amount of organic by-products introduced from other processes (for example, acetic acid) may be included. However, considering the absorption efficiency of (meth)acrylic acid, it is preferable that organic by-products may be included in the content of 15 wt % or less in the absorption solvent fed to the absorption tower (100) (particularly, in the recycled process water).

Furthermore, according to the embodiment of the invention, a raffinate solution that is obtained in a (meth)acrylic acid extraction column (200) as described below may be recycled to a (meth)acrylic acid absorption tower (100) and used as an absorption solvent. Particularly, it is more advantageous in terms of improvement in process efficiency that the raffinate solution is fed to at least one point corresponding to 10 to 30% from the uppermost part of the absorption tower (100), which will be explained in detail with regard to a (meth)acrylic acid extraction column (200) below.

Further, the (meth)acrylic acid absorption tower (100) may be operated at an internal pressure of 1 to 1.5 bar or 1 to 1.3 bar, and at an internal temperature of 50 to 100° C. or 50 to 80° C., considering condensation conditions and moisture content according to saturated water vapor pressure, and the like.

Meanwhile, in the absorption process, a (meth)acrylic acid aqueous solution is discharged to the lower part of the (meth)acrylic acid absorption tower (100), and (meth)acrylic acid-stripped non-condensable gas is discharged to the upper part thereof. Herein, it may be favorable in terms of efficiency of the total process that 40 wt % or more, or 40 to 90 wt %, or 50 to 90 wt % of (meth)acrylic acid may be included in the (meth)acrylic acid aqueous solution.

The obtained (meth)acrylic acid aqueous solution may be fed to a (meth)acrylic acid extraction column (200) through an aqueous solution transfer line (102), as shown in the FIGURE. If an extraction process is introduced between a (meth)acrylic acid absorption process and a distillation process as shown in the FIGURE, most absorption solvent included in the (meth)acrylic acid aqueous solution may be removed in the extraction process, thus lowering a treatment load of the distillation process and reducing energy consumption.

Meanwhile, at least a part of the non-condensable gas discharged to the upper part of the (meth)acrylic acid absorption tower (100) may be fed to a process of recovering organic by-products (particularly, acetic acid) included in the non-condensable gas, and the remainder may be fed to a waste gas incinerator and discarded. Namely, according to one embodiment of the invention, a process of contacting the non-condensable gas with an absorption solvent to recover acetic acid included in the non-condensable gas may be progressed.

The process of contacting the non-condensable gas with an absorption solvent may be conducted in an acetic acid absorption tower (150). As a non-limiting example, an absorption solvent (process water) for absorbing acetic acid may be fed to the upper part of the acetic acid absorption tower (150), and an aqueous solution containing acetic acid may be discharged to the lower part of the acetic acid absorption tower (150). Further, the acetic acid-containing aqueous solution may be fed to the upper part of the (meth)acrylic acid absorption tower (100) and used as an absorption solvent. In addition, acetic acid-stripped non-condensable gas may be recycled to the synthesis process of (meth)acrylic acid and reused.

Herein, for effective absorption of acetic acid, the acetic acid absorption tower (150) may be operated at the internal pressure of 1 to 1.5 bar or 1 to 1.3 bar, and at the internal temperature of 50 to 100° C. or 50 to 80° C. In addition, specific operation conditions of the acetic acid absorption tower (150) may follow the disclosure of Korean Laid-Open Patent Publication No. 2009-0041355.

(Extraction Process)

Meanwhile, an extraction process wherein a (meth)acrylic acid aqueous solution is contacted with an extraction solvent in an extraction column to obtain a (meth)acrylic acid extract solution and a raffinate solution is conducted. Herein, the (meth)acrylic acid aqueous solution may be prepared by the above-explained absorption process.

The extraction process may be conducted in a (meth)acrylic acid extraction column (200). The (meth)acrylic acid aqueous solution fed to the extraction column (200) contacts with an extraction solvent, and is discharged as an extract solution in which a significant amount of (meth)acrylic acid is dissolved and a raffinate solution that is deprived of a significant amount of (meth)acrylic acid, respectively.

Herein, the extract solution that is in a relatively light phase is obtained through the upper outlet of the extraction column (200), and the raffinate solution that is in a relatively heavy phase is obtained through the lower outlet of the extraction column. Before the raffinate solution is discharged from the extraction column (200), a certain amount thereof remains stationary at the stationary section of the lower part of the extraction column, and a part thereof is discharged to the lower outlet of the extraction column.

As such, by contacting the (meth)acrylic acid aqueous solution with an extraction solvent in an extraction column (200) (namely, extraction with small energy consumption compared to distillation), most water included in the (meth)acrylic acid aqueous solution may be removed. Thereby, a treatment load of the subsequent distillation process may be lowered, thus improving energy efficiency of total process. Furthermore, by lowering treatment load of the distillation process, polymerization of (meth)acrylic acid that may be generated during distillation may be minimized, to secure more improved recovery efficiency of (meth)acrylic acid.

Meanwhile, the raffinate solution obtained in the extraction process is recycled to the above-explained absorption process as an absorption solvent. Particularly, according to the embodiment of the invention, the raffinate solution may be fed to at least one point corresponding to 10 to 30%, or 10 to 25%, or 15 to 30%, or 10 to 20%, or 15 to 25% from the uppermost part, instead of the uppermost part of the (meth)acrylic acid absorption tower (100). Further simultaneously, the weight ratio (S/F) of the extraction solvent to the (meth)acrylic acid aqueous solution (i.e., feed) fed to the extraction column (200) may be controlled to greater than 0.3 and less than 1.0, or greater than 0.3 and 0.8 or less, or 0.5 or more and less than 1.0, or 0.5 or more and 0.8 or less.

As such, by recycling the raffinate solution obtained through the extraction process to a specific point of the absorption tower (100) and simultaneously controlling the weight ratio (S/F) of the extraction solvent, the amount of the extraction solvent used and process energy consumption may be remarkably reduced. Namely, through the above-explained process conditions, the recovery method of the above embodiment may minimize loss of (meth)acrylic acid in the absorption process and the extraction process even with a smaller amount of extraction solvent and lower energy consumption. Further, solvent reflux may be increased in the subsequent distillation process, thus further increasing recovery efficiency of (meth)acrylic acid.

In the extraction process, if the weight ratio (S/F) of the extraction solvent to the feed is 0.3 or less, removal efficiency of the absorption solvent in the extraction process may be lowered, and long time operation may be impossible, and thus the effect of introducing the extraction process may become insignificant. Further, if the weight ratio (S/F) of the extraction solvent to the feed is 1.0 or more, the effect of reducing energy consumption may become insignificant. Particularly, as the weight ratio (S/F) increases, although extraction efficiency may be improved, loss of (meth)acrylic acid may increase in the subsequent distillation process, and solvent reflux for preventing this may become excessively high, which is not preferable.

Meanwhile, the point of feeding the raffinate solution to the (meth)acrylic acid absorption tower (100) may be determined considering the part where substantial absorption is achieved, according to the kind of the absorption tower (100). For example, in case the absorption process is conducted in a packed column type of (meth)acrylic acid absorption tower, the raffinate solution obtained through the extraction process may be fed to at least one point corresponding to 10 to 30% from the uppermost part compared to the total packing height of the (meth)acrylic acid absorption tower. Further, in case the absorption process is conducted in a multistage tray type (meth)acrylic acid absorption tower, the raffinate solution obtained through the extraction process may be fed to at least one point corresponding to 10 to 30% from the uppermost stage compared to the total stage number of the (meth)acrylic acid absorption tower.

Herein, in case the raffinate solution is fed to a point exceeding 30% from the uppermost part of the absorption tower (100), absorption efficiency may be lowered, and loss of (meth)acrylic acid through the raffinate solution may increase in the extraction process, thus lowering total process efficiency. Further, in case the raffinate solution is fed to a point less than 10% from the uppermost part of the absorption tower (100), although absorption efficiency may be improved, organic by-products included in the raffinate solution may not be sufficiently recovered in the absorption tower (100).

Meanwhile, it is preferable that the extraction solvent fed to the extraction column (200) may have solubility and hydrophobicity to (meth)acrylic acid. Further, considering the kind of solvent and the properties required in the subsequent distillation process, it is preferable that the extraction solvent may have a lower boiling point than (meth)acrylic acid. For example, the extraction solvent may be a hydrophobic solvent having a boiling point of 120° C. or less, or 10 to 120° C., or 50 to 120° C.

Specifically, the extraction solvent may be at least one selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

According to one embodiment of the invention, it is favorable for securing extraction efficiency that the temperature of the (meth)acrylic acid aqueous solution fed to the extraction column (200) may be 10 to 70° C.

As the extraction column (200), common extraction columns of a liquid-liquid contact type may be used without specific limitations. As non-limiting examples, the extraction column (200) may be a Karr-type reciprocating plate column, a rotary-disk contactor, a Scheibel column, a Kuhni column, a spray extraction tower, a packed extraction tower, a pulsed packed column, and the like.

Through the extraction process, a (meth)acrylic acid extract solution is discharged to the upper part of the extraction column (200), and the discharged extract solution is fed to a distillation column (300) through a transfer line (203). Further, a raffinate solution is discharged to the lower part of the extraction column (200), and the discharged raffinate solution is recycled to a specific point of the (meth)acrylic acid absorption tower (100) through a transfer line (201).

Herein, in the extract solution, in addition to the desired compound (meth)acrylic acid, an extraction solvent, water, and organic by-products may be included. According to one embodiment, at a steady state where stable operation is conducted, 30 to 60 wt % of (meth)acrylic acid, 30 to 60 wt % of an extraction solvent, 3 to 10 wt % of water, and a remaining amount of organic by-products may be included in the extract solution. Namely, most water (for example, 90 wt % or more of water included in the aqueous solution) included in the (meth)acrylic acid aqueous solution may be recovered as a raffinate solution through the extraction process.

As most water is recovered from the extraction column (200), the distillation load of a distillation column (300) may be reduced to lower energy consumption. Further, since distillation conditions may be relaxed, polymerization of (meth)acrylic acid may be minimized in the distillation process, thus securing operation stability and improving recovery efficiency of (meth)acrylic acid.

The raffinate solution discharged from the extraction column (200) may mainly consist of water, but may include non-extracted (meth)acrylic acid. However, according to one embodiment of the invention, 15 wt % or less, or 3 to 15 wt % of (meth)acrylic acid may be included in the raffinate solution, thus minimizing the loss of (meth)acrylic acid in the absorption process and the extraction process.

(Distillation Process)

A distillation process wherein a feed including the (meth) acrylic acid extract solution is distilled to obtain (meth) acrylic acid is conducted.

According to one embodiment of the invention, the feed may be a (meth)acrylic acid extract solution fed from the above-explained extraction process. In this case, the feed is fed to a distillation column (300) through a (meth)acrylic acid extract solution transfer line (203), as shown in the FIGURE.

As explained above, according to the previous recovery method of (meth)acrylic acid, the (meth)acrylic acid aqueous solution obtained in the (meth)acrylic acid absorption tower (100) is fed to the distillation column (300) and distilled.

To the contrary, according to the recovery method of one embodiment of the invention, the (meth)acrylic acid aqueous solution is fed to the (meth)acrylic acid extraction column (200) and extracted, and then the extract solution with a minimized water content is distilled in the distillation column (200). Thereby, the treatment load in the distillation process may be lowered. Further, the temperature around the introduction part of the extract solution in the distillation column (300) may be maintained low, thus minimizing polymerization of (meth)acrylic acid during the distillation process, and enabling more stable operation of the continuous process. Moreover, energy consumption in the distillation process may be remarkably reduced, thus further improving energy efficiency of the total process.

Herein, for effective distillation, it is advantageous that a feed point to which the feed is supplied may be a central part of the distillation column (300), and preferably, it may be any one point corresponding to 40 to 60% of total stages from the uppermost stage of the distillation column (300).

As the feed supplied to the distillation column (300) contacts an azeotropic solvent introduced into the upper part of the distillation column (300), and is heated to an optimum temperature, distillation by evaporation and condensation is achieved.

Herein, in order to effectively separate (meth)acrylic acid included in the feed from the remaining components (for example, water, acetic acid, extraction solvents, and the like), the distillation is preferably conducted by azeotropic distillation.

A solvent used for the azeotropic distillation is preferably a hydrophobic azeotropic solvent that may form an azeotrope with water and acetic acid, and may not form an azeotrope with (meth)acrylic acid. Further, the hydrophobic azeotropic solvent preferably has a lower boiling point than (meth)acrylic acid (for example, a boiling point of 120° C. or less, or 10 to 120° C., or 50 to 120° C.).

Specifically, the hydrophobic azeotropic solvent may be at least one selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

In addition, considering the production efficiency according to the continuous process, it is preferable that the hydrophobic azeotropic solvent is the same as the extraction solvent of the extraction process. As such, if the same kind of solvent is used in the extraction process and the distillation process, at least a part of the solvent that is distilled in the distillation column (300) and recovered through a phase separation tank (350) may be fed to the (meth)acrylic acid extraction column (200) and recycled as an extraction solvent.

Through the distillation process, among the feed, components other than (meth)acrylic acid are discharged to the upper part of the distillation column (300) together with the azeotropic solvent, and (meth)acrylic acid is discharged to the lower part of the distillation column (300).

The upper discharged solution of the distillation column (300) may be fed to the phase separation tank (350) and reused after a predetermined treatment. The phase separation tank (350) is an apparatus for separating immiscible liquids by gravity or centrifugal force and the like, wherein a relatively light liquid (for example, an organic phase) may be recovered from the upper part of the phase separation tank (350), and a relatively heavy liquid (for example, an aqueous phase) may be recovered from the lower part of the phase separation tank (350).

For example, the upper discharged solution of the distillation column (300) may be separated into an organic phase including an azeotropic solvent and an aqueous phase including water in the phase separation tank (350). The separated organic phase may be fed to the upper part of the distillation column (300) and used as an azeotropic solvent, and if necessary, at least a part of the organic phase may be fed to the extraction column (200) and used as an extraction solvent. Further, at least a part of the aqueous phase separated in the phase separation tank (350) may be fed to the (meth)acrylic acid absorption tower (100) and used as an absorption solvent, and a part thereof may be treated as waste water.

In the aqueous phase, acetic acid may be partly included, and the concentration of acetic acid included in the aqueous phase may vary according to the kind of azeotropic solvents and reflux ratio and the like. As non-limiting examples, the concentration of acetic acid included in the aqueous phase may be 1 to 50 wt %, or 2 to 40 wt %, or 3 to 30 wt %.

Meanwhile, while the (meth)acrylic acid aqueous solution passes through the (meth)acrylic acid absorption tower (100), extraction column (200), distillation column (300), and the like, at least a part of (meth)acrylic acid included in the aqueous solution may form dimers or oligomers. To minimize such polymerization of (meth)acrylic acid, common polymerization inhibitors may be added to the distillation column (300).

Further, in the lower discharged solution of the distillation column (300), in addition to (meth)acrylic acid, heavies such as polymers of (meth)acrylic acid, polymerization inhibitors, and the like may be included. Thus, if necessary, a step of feeding the lower discharged solution of the distillation column (300) to a heavies separation tower (400) and separating heavies included in the lower discharged solution may be further conducted. In addition, crude (meth)acrylic acid (CAA) recovered through the process may be passed through an additional crystallization process and obtained as high purity (meth)acrylic acid (HPAA). Herein, the heavies separation process and the crystallization process and the like may be conducted under common conditions, and the process conditions are not specifically limited.

Meanwhile, in the method of continuous recovery of (meth)acrylic acid, each above-explained step may be conducted organically and continuously. Further, in addition to the above-explained steps, processes that can be commonly conducted before or after or simultaneously with each step may be further included.

In the method of continuous recovery of (meth)acrylic acid according to the embodiment of the invention, the above-explained processes may be organically and continuously conducted. Further, in addition to the above-explained processes, processes that can be commonly conducted before or after each process may be further conducted. For example, a process of feeding the (meth)acrylic acid aqueous solution obtained in the (meth)acrylic acid absorption tower (100) to a separate stripping tower before feeding to the (meth)acrylic acid extraction column (200), to remove light ends (acrolein, propionaldehyde, acetaldehyde, formaldehyde, isopropyl acetate, and the like) may be additionally conducted.

II. An Apparatus for Continuous Recovery of (Meth)Acrylic Acid

According to another embodiment of the invention, as shown in the FIGURE, an apparatus for continuous recovery of (meth)acrylic acid is provided, including:

a (meth)acrylic acid absorption tower (100) equipped with a mixed gas inlet to which a mixed gas including (meth)acrylic acid, organic by-products, and vapor, which is produced by a synthesis reaction of (meth)acrylic acid, is fed, and an aqueous solution outlet from which a (meth)acrylic acid aqueous solution obtained by contact of the mixed gas with water is discharged;

a (meth)acrylic acid extraction column (200) equipped with an aqueous solution inlet connected with the aqueous solution outlet of the absorption tower (100) through an aqueous solution transfer line (102), an extract outlet from which the (meth)acrylic acid extract solution obtained by contact of the introduced (meth)acrylic acid aqueous solution with an extraction solvent is discharged, and a raffinate outlet from which the raffinate solution is discharged; and a distillation column (300) equipped with an extract inlet connected with the extract outlet of the extraction column (200) through an extract transfer line (203), and a (meth)

acrylic acid outlet from which (meth)acrylic acid obtained by distillation of the introduced extract solution is discharged, wherein the raffinate outlet of the extraction column (200) is connected to at least one point corresponding to 10 to 30% from the uppermost part of the absorption tower (100) through a raffinate transfer line (201), and the apparatus is operated such that the weight ratio of the extraction solvent to the (meth)acrylic acid aqueous solution fed to the extraction column (200) is greater than 0.3 and less than 1.0.

Specifically, in the apparatus of the above embodiment, the (meth)acrylic acid absorption tower (100) is connected to the (meth)acrylic acid extraction column (200) through a (meth)acrylic acid aqueous solution transfer line (102). Further, the (meth)acrylic acid extraction column (200) is connected to the distillation column (300) through a (meth)acrylic acid extract transfer line (203).

Particularly, the apparatus of the above embodiment includes a raffinate transfer line (201) connected such that the raffinate solution obtained in the (meth)acrylic acid extraction column (200) is fed to at least one point corresponding to 10 to 30% from the uppermost part of the (meth)acrylic acid absorption tower (100).

The kind of the (meth)acrylic acid absorption tower (100) may be determined considering contact efficiency of the mixed gas (1) with the absorption solvent. As a non-limiting example, the (meth)acrylic acid absorption tower (100) may be a packed column type of absorption tower, a multistage tray type of absorption tower, and the like. Inside the packed column type absorption tower, fillers such as a Raschig ring, a pall ring, a saddle, gauze, structured packing, and the like may be applied.

Herein, in case the (meth)acrylic acid absorption tower (100) is a packed column type of absorption tower, the raffinate outlet of the extraction column (200) is connected to at least one point corresponding to 10 to 30% from the uppermost part compared to the total packing height of the absorption tower (100) through the raffinate transfer line (201).

Further, in case the (meth)acrylic acid absorption tower (100) is a multistage tray type of absorption tower, the raffinate outlet of the extraction column (200) is connected to at least one point corresponding to 10 to 30% from the uppermost stage compared to the total stage number of the absorption tower (100) through the raffinate transfer line (201).

As the (meth)acrylic acid extraction column (200), common extraction columns of a liquid-liquid contact type may be used without specific limitation. As non-limiting examples, the extraction column may be a Karr-type reciprocating plate column, a rotary-disk contactor, a Scheibel column, a Kuhni column, a spray extraction column, a packed extraction tower, a pulsed packed column, and the like.

Further, the distillation column (300) may be a packed column including fillers inside or a multistage column, preferably a sieve tray column, or a dual flow tray column, and the like.

In addition, the acetic acid absorption tower (150), (meth)acrylic acid aqueous solution transfer line (102), extract transfer line (203), phase separation tank (350), heavies separation tower (400), and the like may have constructions common in the technical field to which the invention pertains.

Hereinafter, preferable examples are presented to aid in understanding of the invention. However, these examples are only to illustrate the invention, and the scope of the invention is not limited thereto.

Example 1

Using an apparatus with the construction as shown in the FIGURE and an Aspen Plus process simulator (Aspen Technology, Inc.), a process of continuously recovering acrylic acid was conducted as follows.

(Absorption Process)

Mixed gas obtained through the oxidation of propylene was prepared. The composition of the mixed gas was about 16.6 wt % of acrylic acid, about 0.3 wt % of acrolein, about 0.5 wt % of acetic acid, about 0.3 wt % of non-reacted propylene, about 2.6 wt % of carbon monoxide and carbon dioxide, about 10.1 wt % of water vapor, about 69.1 wt % of nitrogen and oxygen, and about 0.3 wt % of heavies.

The acrylic acid absorption tower (100) is a tray tower with a total number of theoretical stages of 10, and the internal temperature was controlled to 50 to 100° C. The mixed gas was fed to the lowermost stage of the absorption tower (100) at a temperature of about 160° C., a pressure of about 1.3 bar, and a mass flow of about 62,860 kg/h. Further, process water, which is an absorption solvent of acrylic acid, was fed to the $2^{nd}$ stage from the uppermost stage of the absorption tower (100) (the $2^{nd}$ stage among the total of 10 stages).

Further, from the lower part of the absorption tower (100), an acrylic acid aqueous solution (composition: about 66.1 wt % of acrylic acid, about 4.2 wt % of acetic acid, about 28.4 wt % of water, about 1.3 wt % of others) was obtained at a mass flow of about 15,814 kg/h. The acrylic acid aqueous solution was fed to an acrylic acid extraction column (200) through a transfer line (102).

(Extraction Process)

An acrylic acid extraction column (200) is a tray tower with a total number of theoretical stages of 5, and an acrylic acid aqueous solution was introduced to the uppermost stage.

Further, a part of reflux flow including toluene obtained as an organic layer in the upper discharged solution of a distillation column (300) was used as an extraction solvent of the extraction column (200). Herein, the weight ratio (S/F) of the extraction solvent to the acrylic acid aqueous solution was controlled to about 0.7.

After conducting stable operation, at a steady state, an extract solution was obtained from the upper part of the extraction column (200), and a raffinate solution was obtained from the lower part of the extraction column (200). The mass flow and the concentration of each flow at the steady state operation of the extraction column (200) are shown in the following Table 1.

TABLE 1

|  |  | Extraction solvent | Acrylic acid aqueous solution | Extract solution | Raffinate solution |
| --- | --- | --- | --- | --- | --- |
| Mass Flow (kg/h) |  | 11,070 | 15,814 | 23,227 | 3657 |
| Composition (wt %) | Toluene | 99.3 | 0 | 47.3 | 0.1 |
|  | Acrylic acid | 0.4 | 66.1 | 44.3 | 5.9 |
|  | Acetic acid | 0.3 | 4.2 | 2.4 | 3.8 |
|  | Water | 0 | 28.4 | 5.4 | 88.1 |
|  | Others | 0 | 1.3 | 0.6 | 2.1 |

As shown in Table 1, it was confirmed that the content of acrylic acid included in the raffinate solution was about 5.9 wt %, and the content of toluene included in the extract solution is about 47.3 wt %. Further, a water removal rate in the extraction column (200) was measured to be about 71.8%.

The extract solution was fed to a distillation column (300) through a transfer line (203). Further, the raffinate solution was fed to the $2^{nd}$ stage from the uppermost stage of the absorption tower (100) ($2^{nd}$ stage among the total of 10 stages) and reused as an absorption solvent. Herein, the amount of acrylic acid that was discharged to the upper part of the absorption tower (100) and lost was 135.9 kg/h.

(Distillation Process)

A distillation column (300) is a tray tower with a total number of theoretical stages of 20, and the operation pressure was maintained at about 110 torr. The extract solution was introduced to the $9^{th}$ stage from the uppermost stage of the distillation column (300) at a mass flow of about 23,227 kg/h. Further, a part of toluene reflux flow separated in the phase separation tank (350) was introduced into the uppermost stage, the $1^{st}$ stage of the distillation column (300). Further, from the upper stage of the distillation column (300), toluene, water, and acetic acid included in the extract solution were discharged, and from the lower stage, acrylic acid was discharged.

Herein, toluene reflux flow fed to the distillation column (300) was controlled to about 16,578 kg/h, so that the total toluene flow fed to the distillation column may be the same as that in case only absorption-distillation processes are conducted without the extraction process (namely, so that the total amount of toluene fed to the distillation column may be the same).

Further, in the phase separation tank (350), the concentration of acrylic acid included in the organic layer was confirmed to be about 0.9 wt %, and the concentration of acrylic acid included in the aqueous layer was confirmed to be about 0.8 wt %.

Energy consumed in the distillation column (300) was about 3.8 Gcal/h. For reference, in case only absorption-distillation processes are conducted without the extraction process, energy consumed in the distillation process is about 5.8 Gcal/h. In comparison, according to Example 1, energy reduction rate in the distillation column (300) is about 34.5%.

Through the above continuous process, among about 10,723 kg/h of acrylic acid fed to the absorption tower (100), about 10,116 kg/h of acrylic acid was recovered from the lower part of the distillation column (300), and a one pass recovery rate of acrylic acid was about 94.3%. Herein, the "one pass recovery rate" means a recovery rate when acrylic acid loss generated in each unit process is not recovered.

Example 2

The absorption process and extraction process were conducted by the same method as Example 1.

However, in the distillation process, among the toluene reflux flow fed to the distillation column (300), the content of toluene was controlled to be larger than in Example 1, and the toluene reflux flow was shown to be about 25,000 kg/h.

Further, in the phase separation tank (350), the concentration of acrylic acid included in the organic layer was confirmed to be about 0.6 wt %, and the concentration of acrylic acid included in the aqueous layer was confirmed to be about 0.6 wt %.

Energy consumed in the distillation column (300) was about 4.7 Gcal/h, which shows an energy reduction rate of about 19.0% compared to a method without the extraction process.

Through the above continuous process, among about 10,723 kg/h of acrylic acid fed to the absorption tower (100), about 10,167 kg/h of acrylic acid was recovered from the lower part of the distillation column (300), and the one pass recovery rate of acrylic acid was shown to be about 94.8%.

Example 3

The absorption process and extraction process were conducted by the same method as Example 1.

However, in the distillation process, among the toluene reflux flow fed to the distillation column (300), the content of toluene was controlled to be smaller than in Example 1, and the toluene reflux flow was shown to be about 10,000 kg/h.

Further, in the phase separation tank (350), the concentration of acrylic acid included in the organic layer was confirmed to be about 1.0 wt %, and the concentration of acrylic acid included in the aqueous layer was confirmed to be about 1.0 wt %.

In addition, energy consumed in the distillation column (300) was about 3.1 Gcal/h, which shows an energy reduction rate of about 46.6% compared to a method without the extraction process.

Through the above continuous process, among about 10,723 kg/h of acrylic acid fed to the absorption tower (100), about 10,098 kg/h of acrylic acid was recovered from the lower part of the distillation column (300), and the one pass recovery rate of acrylic acid was shown to be about 94.2%.

Comparative Example 1

The absorption process was conducted by the same method as Example 1.

However, in the distillation process, the weight ratio (S/F) of the extraction solvent to the acrylic acid aqueous solution was controlled to about 0.3. The mass flow and the concentration of each flow at steady state operation of the extraction column (200) are shown in the following Table 2.

TABLE 2

| | | Extraction solvent | Acrylic acid aqueous solution | Extract solution | Raffinate solution |
|---|---|---|---|---|---|
| Mass Flow (kg/h) | | 6000 | 15,814 | 18,707 | 3107 |
| Composition (wt %) | Toluene | 99.3 | 0 | 31.8 | 0.1 |
| | Acrylic acid | 0.4 | 66.1 | 54.3 | 10.4 |
| | Acetic acid | 0.3 | 4.2 | 3.0 | 3.9 |
| | Water | 0 | 28.4 | 10.1 | 83.7 |
| | Others | 0 | 1.3 | 0.8 | 1.9 |

In the case of Comparative Example 1, water removal efficiency in the extraction column (200) (removal rate of about 58.0%) decreased compared to Example 1 (removal rate of about 71.8%), and thus long time operation was not possible. Further, in the case of Comparative Example 1, the content of acrylic acid included in the raffinate solution was as high as about 10.4 wt %, thus showing larger acrylic acid loss compared to Example 1.

Comparative Example 2

(Absorption Process)

The absorption process was conducted by the same method as Example 1, except that the acrylic acid absorption solvent of process water and the raffinate solution obtained from the extraction process were fed to the uppermost stage of the absorption tower (100).

(Extraction Process)

The extraction process was conducted by the same method as Example 1, except that the weight ratio (S/F) of the extraction solvent to the acrylic acid aqueous solution was controlled to about 2. The mass flow and the concentration of each flow at steady state operation of the extraction column (200) are shown in the following Table 3.

TABLE 3

|  |  | Extraction solvent | Acrylic acid aqueous solution | Extract solution | Raffinate solution |
|---|---|---|---|---|---|
| Mass Flow (kg/h) |  | 31,628 | 15,814 | 43,294 | 4148 |
| Composition (wt %) | Toluene | 99.3 | 0 | 72.5 | 0.1 |
|  | Acrylic acid | 0.4 | 66.1 | 24.3 | 1.6 |
|  | Acetic acid | 0.3 | 4.2 | 1.4 | 3.5 |
|  | Water | 0 | 28.4 | 1.5 | 92.5 |
|  | Others | 0 | 1.3 | 0.3 | 2.3 |

In the case of Comparative Example 2, water removal efficiency in the extraction column (200) (removal rate of about 88.5%) was superior to Example 1, and the content of acrylic acid included in the raffinate solution was as low as about 1.6 wt %, thus showing smaller acrylic acid loss compared to Example 1.

The extract solution was fed to the distillation column (300) through a transfer line (203). Further, the raffinate solution was fed to the uppermost stage of the absorption tower (100) at a mass flow of 3000 kg/h and reused as an absorption solvent. Herein, the amount of acrylic acid that was discharged to the upper part of the absorption tower (100) and lost was shown to be 73.0 kg/h.

(Distillation Process)

The extract solution was introduced to the $9^{th}$ stage from the uppermost stage of the distillation column (300) identical to Example 1 at a mass flow of about 43,294 kg/h. A part of toluene reflux flow separated in the phase separation tank (350) was introduced into the uppermost stage, the $1^{st}$ stage of the distillation column (300). From the upper stage of the distillation column (300), toluene, water, and acetic acid included in the extract solution were discharged, and from the lower stage, acrylic acid was discharged.

Herein, toluene reflux flow fed to the distillation column (300) was controlled to about 7158 kg/h, so that the total toluene flow fed to the distillation column may be the same as that in case only absorption-distillation processes are conducted without the extraction process (namely, so that the total amount of toluene fed to the distillation column may be the same).

In the phase separation tank (350), the concentration of acrylic acid included in the organic layer was confirmed to be about 3.1 wt %, and the concentration of acrylic acid included in the aqueous layer was confirmed to be about 3.0 wt %, which are higher than the concentration of acrylic acid lost to the phase separation tank (350) in Example 1. Thus, in the case of Comparative Example 2, in order to prevent loss of acrylic acid, excessive toluene reflux flow was required.

Energy consumed in the distillation column (300) was about 4.7 Gcal/h, thus showing an energy reduction rate of about 19.0% compared to the case wherein only absorption-distillation processes are conducted without the extraction process.

Through the above continuous process, among about 10,723 kg/h of acrylic acid fed to the absorption tower (100), about 9263 kg/h of acrylic acid was recovered from the lower part of the distillation column (300), and the one pass recovery rate of acrylic acid was about 86.4%.

In summary, in the case of Comparative Example 2, although extraction efficiency was superior to Example 1, acrylic acid loss in the distillation column increased. Thus, excessive toluene reflux flow was required for preventing acrylic acid loss, and energy consumption in the distillation process was shown to be high. Further, in the case of Comparative Example 1, the acrylic acid recovery rate compared to energy consumption was shown to be low compared to Example 1.

Comparative Example 3

The absorption process was conducted by the same method as Example 1, except that the acrylic acid absorption solvent of process water and the raffinate solution obtained from the extraction process were fed to the uppermost stage of the absorption tower (100). The extraction process and the distillation process were conducted by the same method as Example 1.

The raffinate solution fed to the absorption tower (100) in the extraction process was fed to the uppermost stage of the absorption tower (100) at a mass flow of 3000 kg/h and reused as an absorption solvent.

Herein, the amount of acrylic acid that was discharged to the upper part of the absorption tower (100) and lost was shown to be 151.0 kg/h. Such acrylic acid loss is about a 10% increase even compared to Comparative Example 1.

Comparative Example 4

The absorption process was conducted by the same method as Example 1 (the raffinate solution of the extraction process was fed to the $2^{nd}$ stage of the absorption tower).

(Extraction Process)

The extraction process was conducted by the same method as Example 1, except that the weight ratio (S/F) of the extraction solvent to the acrylic acid aqueous solution was controlled to about 1. The mass flow and the concentration of each flow at steady state operation of the extraction column (200) are shown in the following Table 4.

TABLE 4

|  |  | Extraction solvent | Acrylic acid aqueous solution | Extract solution | Raffinate solution |
|---|---|---|---|---|---|
| Mass Flow (kg/h) |  | 15,814 | 15,814 | 27,848 | 3780 |
| Composition (wt %) | Toluene | 99.3 | 0 | 56.4 | 0.1 |
|  | Acrylic acid | 0.4 | 66.1 | 37.5 | 2.2 |
|  | Acetic acid | 0.3 | 4.2 | 2.1 | 3.7 |
|  | Water | 0 | 28.4 | 3.6 | 91.9 |
|  | Others | 0 | 1.3 | 0.4 | 2.1 |

In the case of Comparative Example 4, water removal efficiency in the extraction column (200) (removal rate of about 77.4%) was superior to Example 1 (removal rate of about 71.8%), and the content of acrylic acid included in the raffinate solution was shown to be low compared to Example 1.

The extract solution was fed to the distillation column (300) through a transfer line (203). Further, the raffinate solution was fed to the $2^{nd}$ stage of the absorption tower (100) at a mass flow of 3000 kg/h and reused as an absorption solvent. Herein, the amount of acrylic acid that was discharged to the upper part of the absorption tower (100) and lost was shown to be 95.5 kg/h.

(Distillation Process)

The extract solution was introduced into the $9^{th}$ stage from the uppermost stage of the distillation column (300) identical to Example 1 at a mass flow of about 27,848 kg/h. Further, a part of toluene reflux flow separated in the phase separation tank (350) was introduced into the uppermost stage, the $1^{st}$ stage of the distillation column (300). From the upper stage of the distillation column (300), toluene, water, and acetic acid included in the extract solution were discharged, and acrylic acid was discharged from the lower stage.

Herein, toluene reflux flow fed to the distillation column (300) was controlled to about 29,000 kg/h, so that the reflux ratio may be the same as Example 2 (reflux ratio of about 1.9).

In the phase separation tank (350), the concentration of acrylic acid included in the organic layer was confirmed to be about 0.7 wt %, and the concentration of acrylic acid included in the aqueous layer was confirmed to be about 0.7 wt %, which are a little higher than the concentration of acrylic acid lost to the phase separation tank (350) in Example 2.

Energy consumed in the distillation column (300) was about 5.3 Gcal/h, thus showing an energy reduction rate of about 8.6% compared to the case wherein only absorption-distillation processes are conducted without the extraction process.

Through the above continuous process, among about 10,723 kg/h of acrylic acid fed to the absorption tower (100), about 10,224 kg/h of acrylic acid was recovered from the lower part of the distillation column (300), and the one pass recovery rate of acrylic acid was about 95.3%.

In summary, in the case of Comparative Example 4, although extraction efficiency was superior to Example 2, acrylic acid loss in the distillation column increased despite the reflux ratio identical to Example 2. In the case of Comparative Example 4, energy consumption in the distillation process was shown to be high compared to Example 2, and Comparative Example 4 showed an energy reduction rate of about 8.6% compared to the method without the extraction process, thus confirming that the effect resulting from the introduction of the extraction process was insignificant.

Comparative Example 5

The absorption process was conducted by the same method as Comparative Example 4, except that the acrylic acid absorption solvent of process water and the raffinate solution obtained from the extraction process were fed to the uppermost stage of the absorption tower (100). The extraction process and the distillation process were conducted by the same method as Comparative Example 4.

The raffinate solution fed to the absorption tower (100) in the extraction process was fed to the uppermost stage of the absorption tower (100) at a mass flow of 3000 kg/h, and reused as an absorption solvent. Herein, the amount of acrylic acid that was discharged to the upper part of the absorption tower (100) and lost was shown to be 88.8 kg/h. Such acrylic acid loss was about a 7% decrease compared to Comparative Example 4.

However, similar to Comparative Example 4, in the case of Comparative Example 5, acrylic acid loss in the distillation column increased despite the reflux ratio identical to Example 2. Further, in Comparative Example 5, energy consumption in the distillation process was shown to be high compared to Example 2, and Comparative Example 5 showed an energy reduction rate of about 8.6% compared to a method without the extraction process, thus confirming that the effect resulting from the introduction of the extraction process was insignificant.

Comparative Example 6

The absorption process and the extraction process were conducted by the same method as Comparative Example 2.

However, in order to decrease acrylic acid loss in the distillation process, among the toluene reflux flow fed to the distillation column (300), the content of toluene was controlled to be larger than Comparative Example 2, and the toluene reflux flow was shown to be about 15,000 kg/h.

Thereby, in the phase separation tank (350), the concentration of acrylic acid included in the organic layer was about 1.9 wt %, and the concentration of acrylic acid included in the aqueous layer was about 1.8 wt %, which are lower than Comparative Example 2, and the one pass recovery rate of acrylic acid slightly increased to 90.1%.

However, energy consumed in the distillation column (300) was about 5.5 Gcal/h, showing an energy reduction rate of about 5.2% compared to the method without the extraction process, and thus it was confirmed that the effect resulting from the introduction of the extraction process was insignificant.

Comparative Example 7

The absorption process and the extraction process were conducted by the same method as Comparative Example 2.

However, in order to further decrease acrylic acid loss in the distillation process, among the toluene reflux flow fed to the distillation column (300), the content of toluene was controlled to be larger than Comparative Example 2, and the toluene reflux flow was shown to be about 25,000 kg/h.

Thereby, in the phase separation tank (350), the concentration of acrylic acid included in the organic layer was about 1.3 wt %, and the concentration of acrylic acid included in the aqueous layer was about 1.2 wt %, which are lower than Comparative Example 2, and the one pass recovery rate of acrylic acid slightly increased to 93.2%.

However, energy consumed in the distillation column (300) was about 6.5 Gcal/h, and thus it was confirmed that more energy was consumed compared to a method without the extraction process.

The invention claimed is:

1. A method for continuous recovery of (meth)acrylic acid, comprising:
  an absorption process wherein a mixed gas including (meth)acrylic acid, organic by-products, and vapor, which is produced by a synthesis reaction of (meth)

acrylic acid, is contacted with water to obtain a (meth) acrylic acid aqueous solution;

an extraction process wherein the (meth)acrylic acid aqueous solution obtained through the absorption process is contacted with an extraction solvent in an extraction column to obtain a (meth)acrylic acid extract solution and a raffinate solution; and a distillation process wherein a feed including the (meth) acrylic acid extract solution obtained through the extraction process is distilled to obtain (meth)acrylic acid, wherein the absorption process is conducted in a packed column type of (meth)acrylic acid absorption tower, a weight ratio of the extraction solvent to the (meth) acrylic acid aqueous solution fed to the extraction column is greater than 0.3 and less than 1.0, and the raffinate solution obtained through the extraction process is fed to at least one point corresponding to 10 to 30% below the uppermost part based on the total height of the column packing within the (meth)acrylic acid absorption tower.

2. A method for continuous recovery of (meth)acrylic acid, comprising:

an absorption process wherein a mixed gas including (meth)acrylic acid, organic by-products, and vapor, which is produced by a synthesis reaction of (meth) acrylic acid, is contacted with water to obtain a (meth) acrylic acid aqueous solution;

an extraction process wherein the (meth)acrylic acid aqueous solution obtained through the absorption process is contacted with an extraction solvent in an extraction column to obtain a (meth)acrylic acid extract solution and a raffinate solution; and a distillation process wherein a feed including the (meth) acrylic acid extract solution obtained through the extraction process is distilled to obtain (meth)acrylic acid, wherein the absorption process is conducted in a multistage tray type of (meth)acrylic acid absorption tower, a weight ratio of the extraction solvent to the (meth) acrylic acid aqueous solution fed to the extraction column is greater than 0.3 and less than 1.0, and the raffinate solution obtained through the extraction process is fed to at least one point corresponding to 10 to 30% below the uppermost stage of the multistage trays present within the (meth)acrylic acid absorption tower based on the total number of stages within the multistage tray type of (meth)acrylic acid absorption tower.

3. The method for continuous recovery of (meth)acrylic acid according to claim 1, wherein the extraction solvent is a hydrophobic solvent having a boiling point of 10 to 120° C.

4. The method for continuous recovery of (meth)acrylic acid according to claim 1, wherein the extraction solvent is at least one selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

5. The method for continuous recovery of (meth)acrylic acid according to claim 1, wherein the extract solution obtained through the extraction process includes 30 to 60 wt % of (meth)acrylic acid, 30 to 60 wt % of an extraction solvent, 3 to 10 wt % of water, and a remaining amount of organic by-products.

6. The method for continuous recovery of (meth)acrylic acid according to claim 1, wherein the raffinate solution obtained through the extraction process includes (meth) acrylic acid in a content of 15 wt % or less.

7. The method for continuous recovery of (meth)acrylic acid according to claim 1, wherein the synthesis reaction of (meth)acrylic acid is an oxidation reaction of at least one compound selected from the group consisting of propane, propylene, butane, isobutylene, and (meth)acrolein in the presence of a gas phase catalyst.

\* \* \* \* \*